United States Patent [19]

Urrutia

[11] Patent Number: 5,725,511
[45] Date of Patent: Mar. 10, 1998

[54] METHOD AND APPARATUS FOR PREVENTION OF BLOOD-TYPE MISMATCHES

[76] Inventor: Sharon A. Urrutia, 105 Vista La., Louisville, Colo. 80027

[21] Appl. No.: 524,753

[22] Filed: Sep. 7, 1995

[51] Int. Cl.⁶ .................................... A61M 25/00
[52] U.S. Cl. ................. 604/280; 604/283; 604/80; 604/905
[58] Field of Search ............... 604/80, 82, 280, 604/283, 905; 285/3, 4, 345, 374, 399

[56] References Cited

U.S. PATENT DOCUMENTS

| | | | |
|---|---|---|---|
| 3,625,212 | 12/1971 | Rosenberg et al. | 128/214 R |
| 4,150,673 | 4/1979 | Watt | 128/272 |
| 5,224,932 | 7/1993 | Lappas | 604/80 |
| 5,334,170 | 8/1994 | Moroski | 604/80 |

Primary Examiner—Corrine M. McDermott
Assistant Examiner—Cris L. Rodriguez
Attorney, Agent, or Firm—Douglass F. Vincent

[57] ABSTRACT

Method and apparatus for preventing mismatching of blood types between a blood bag and a patient. A first connector has a configuration coding corresponding to the blood type of the blood in the bag, and has means for piercing and providing access to the bag. Blood tubing fluidly connects the blood bag to the patient and has a second connector with configuration coding corresponding to the blood type of the patient. The first and second connection must have matching configurations in order to sealably connect and deliver blood to the patient, thereby preventing mismatches. Optionally, another pair of configuration coded connectors may also be provided to sealably connect the intravenous needle in the arm of the patient. These two pairs of configuration coded connectors may be used separately or together to guard against blood type mismatches.

3 Claims, 3 Drawing Sheets

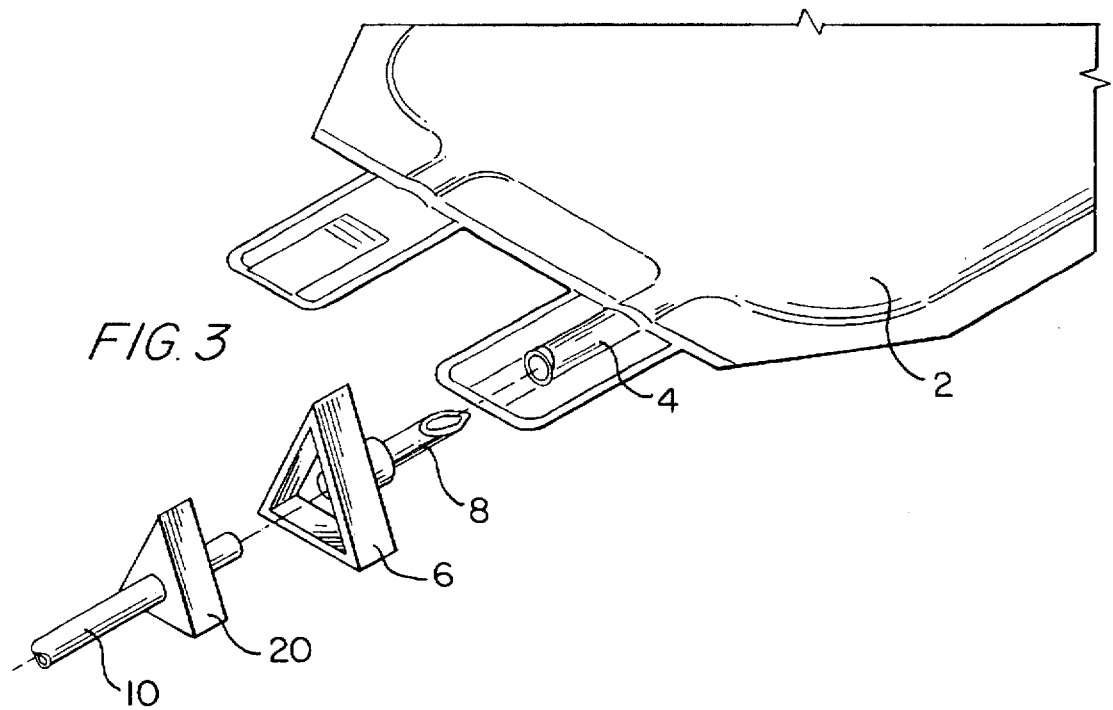
FIG. 3
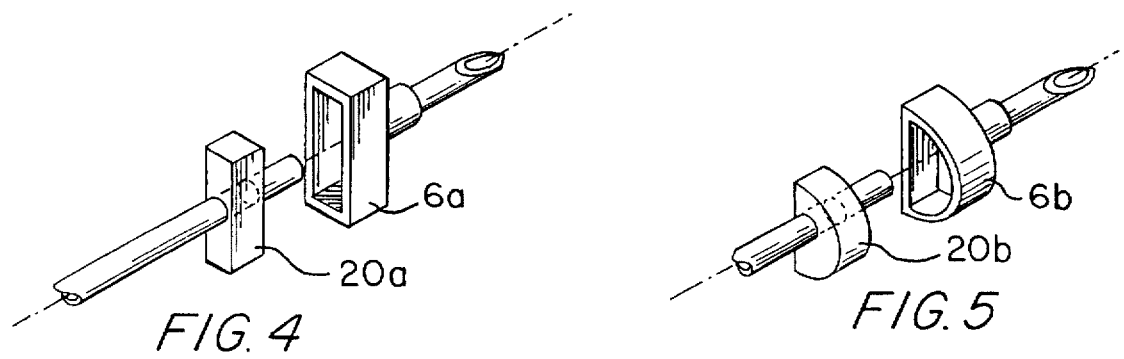
FIG. 4
FIG. 5
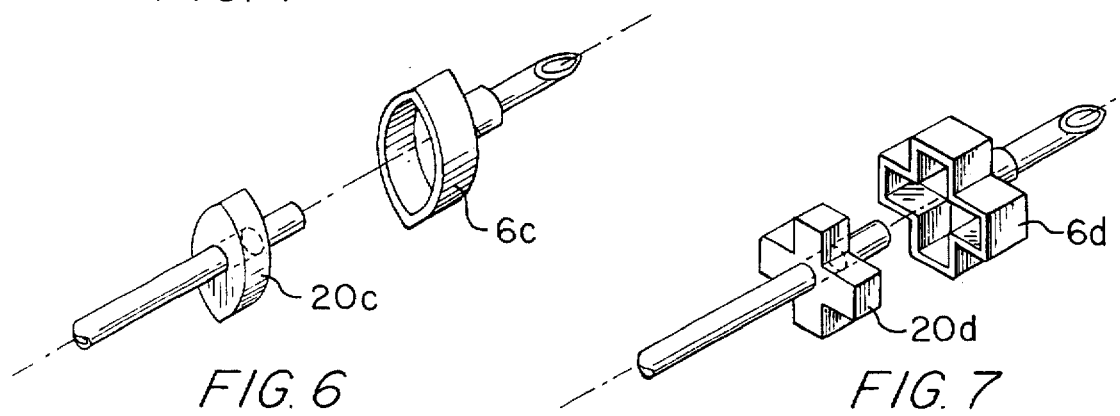
FIG. 6
FIG. 7

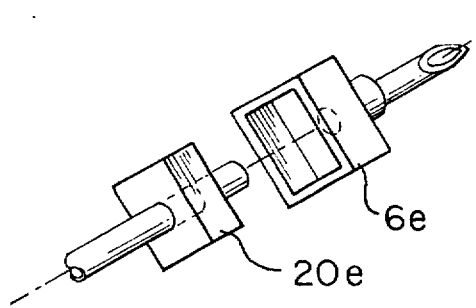
FIG. 8
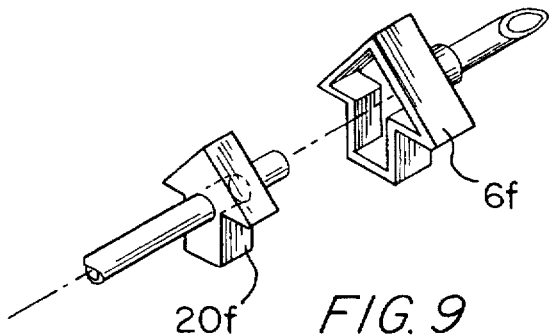
FIG. 9
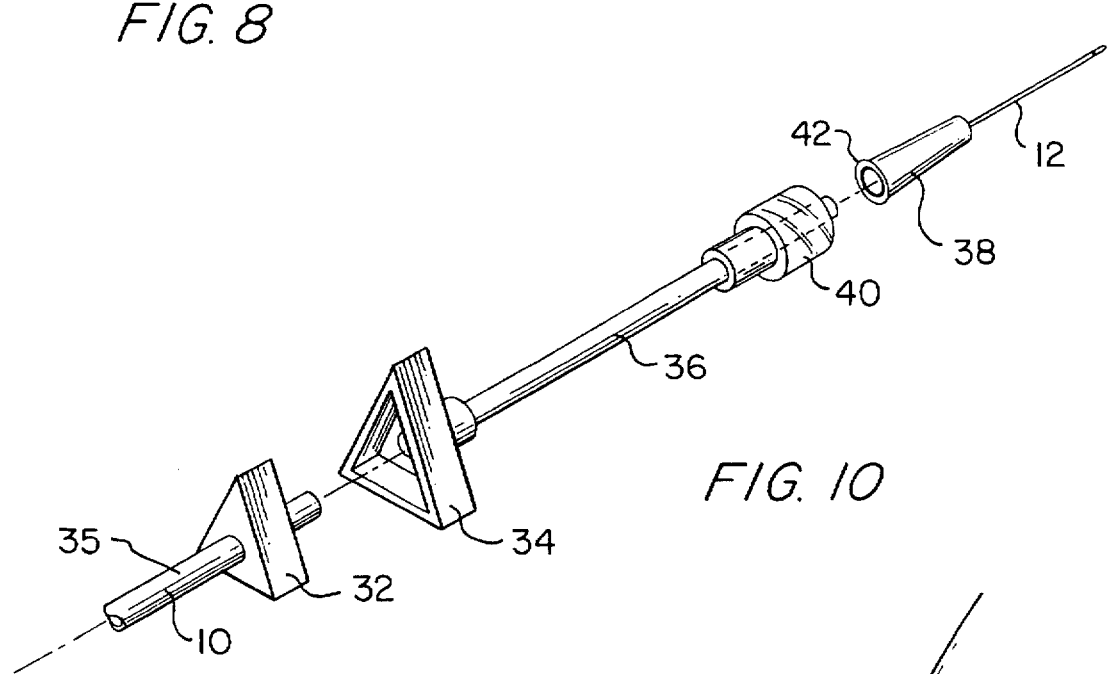
FIG. 10
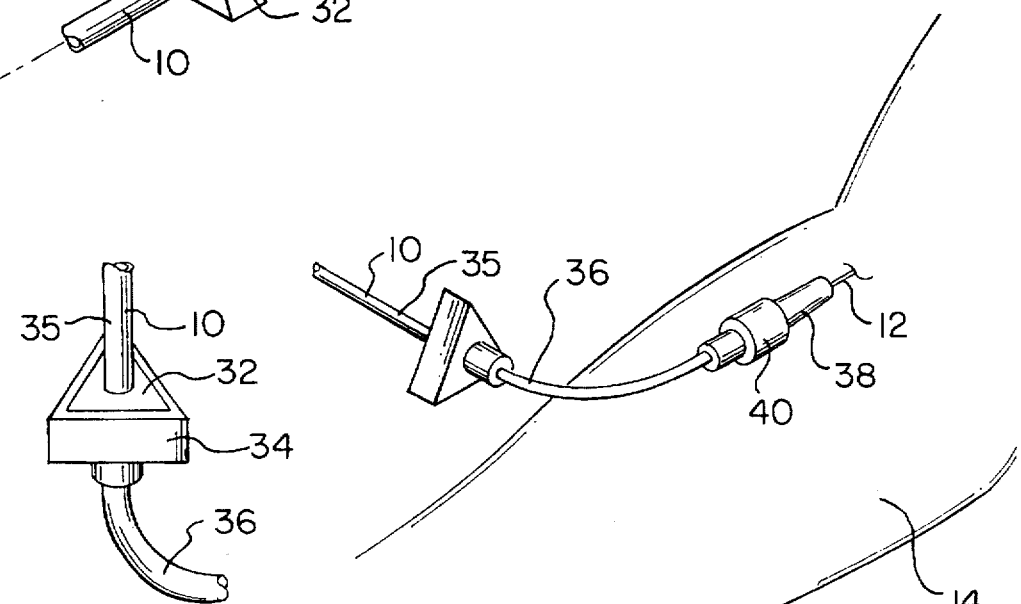
FIG. 12
FIG. 11

METHOD AND APPARATUS FOR PREVENTION OF BLOOD-TYPE MISMATCHES

TECHNICAL FIELD

This invention relates to a method and apparatus for use in connection with blood transfusions, and more particularly to a method and apparatus using configuration-coded connectors to prevent blood type mismatches.

BACKGROUND ART

In delivering blood to a patient intravenously, the blood type of the patient is first carefully checked against the blood type as marked on the blood container, and only then is the blood delivered to the patient. This method of matching the blood type of the patient to that of the blood donor is generally quite effective. Nonetheless, mismatches can be and have been made in using this approach, and such mistakes are most often fatal to the patient. There is therefore a need for an approach which will further reduce mistakes in blood-type matching.

While no reliable safety methods are known for prevent blood-type mismatches generally, various approaches have been tried previously which are aimed at increasing the safety of the process of plasmapheresis. Plasmapheresis is a method of obtaining plasma from a blood donor by extracting blood, centrifuging the blood to remove plasma, and then returning red blood cells to the donor. The mistake to be guarded against in plasmapheresis is that the blood cells would be returned to the wrong donor. U.S. Pat. No. 3,623,212 to Rosenberg discloses a method for avoiding such mistakes in plasmapheresis. Rosenberg employs a mating plug and a receptacle of like shape for connection between the blood bag and its support. Rosenberg's method is well suited for preventing mistakes in plasmapheresis, which typically takes place in a single centralized location. However, blood transfusions are typically given throughout a hospital, and use of Rosenberg's method to prevent blood-type mismatches in transfusions would require that each blood bag support stand throughout a hospital be equipped with a large configuration-coded receptacle, while multiple matching mating plugs would likewise have to be distributed throughout the hospital. Such an approach would be cumbersome and expensive. Additionally, as Rosenberg himself states, his method merely makes mismatches inconvenient, but would not render them impossible. A method is thus needed which cannot be circumvented by well-intentioned personnel who might simply be in a hurry to accomplish their task. U.S. Pat. No. 4,678,458 to Fredeking discloses what may be a more foolproof method of preventing a donor mismatch in plasmapheresis. Fredeking utilizes a key, unique to the donor, which is attached to the blood collector bag prior to centrifuging the blood. After the centrifuging operation, flow between the collection bag and the donor can only be established by utilizing the key in the correct lock. Again, however, this method is best suited for a centralized process such as plasmapheresis, and would be inconvenient to implement on a hospital-wide basis for preventing similar problems with blood transfusions.

U.S. Pat. No. 3,831,625 to Roediger, and U.S. Pat. No. 4,256,132 to Gunter both utilize latches having labels thereon to prevent delivery of an incorrect intravenous medication to a patient. However, both the Roediger and Gunter methods require that the labels be read and correctly followed in order to achieve their intended results, which invites human error. U.S. Pat. No. 4,795,429 to Feldstein also deals with controlling intravenous medications generally. Feldstein uses a variety of visual aids to indicate to personnel which medication is being delivered to the patient, including labels, staggered positioning, and color-coding. However, this approach is also subject to misreading by personnel. U.S. Pat. No. 4,150,673 to Watt discloses a configuration-coded entry system for a blood bag. However, Watt's method is directed toward inlets to the blood bag for receiving additives thereto. Presumably, it is because Watt is concerned with additives to the blood bag that he utilizes a multiple-inlet approach. For example, having five configuration-coded inlets as shown in Watt's drawings would serve to limit the number of potential additives to five, each of which would necessarily come from a source having a matching configuration-coded outlet. However, Watt's approach would be uniquely unsuited for preventing blood-type mismatches, as only one configuration coded outlet from a blood bag could be utilized to effectuate such a purpose. The use of more than one configuration-coded outlet on a blood bag would effectively defeat the purpose of such a system for preventing blood-type mismatching.

Therefore, it is a principal object of the present invention to provide a method and apparatus for reducing the chance of mismatching the blood-type of a patient with the type of blood to be delivered to the patient.

Another object of the present invention is to provide a method and apparatus for preventing blood-type mismatches which may be easily implemented with little change to existing equipment or procedures.

DISCLOSURE OF THE INVENTION

In accordance with this invention a method and apparatus for prevention of blood-type mismatches is provided. In the invention, a first connector has a configuration coding corresponding to a selected blood type. This connector has a sharpened tubular protrusion which is used to pierce the bag and provide access thereto. Blood tubing for connecting the bag to the patient has a second matching configuration-coded connector which sealably connects to the first connector. The connectors corresponding to each of the seven unique blood types are mutually incompatible with one another. This precludes connection between a blood bag having a connector corresponding to the blood type within the bag and blood tubing having a connector with a configuration coding corresponding to another blood type. So long as the configuration coding of at least one of the connectors corresponds to the blood type of the patient, mismatching of blood types to the patient will be physically impossible. Preferably, the second connector would be selected so that its configuration-coding matched the blood type of the patient.

Alternatively, a like set of connectors may be provided at the arm of the patient. In this embodiment, a first connector having a configuration coding corresponding to the blood type of the patient is sealably connectable to the intravenous needle in the patient's arm. A second connector is provided at the patient end of the blood tubing for sealably connecting with the first connector. The second connector has a configuration coding which matches the blood type of the blood bag. In this way, blood type mismatches between the patient and the blood bag are prevented.

Optimally, all four of the above-mentioned connectors may be employed for maximum safety. However, when all four connectors are utilized, only the connector for piercing and providing access to the bag should be configuration-coded to match the blood in the bag. All the other connectors should be selected to match the blood type of the patient, thus providing extra protection against the patient receiving an incorrect blood type.

In view of the foregoing, several advantages of the present invention are readily apparent. A method and apparatus for prevention of blood-type mismatches is provided which, when properly implemented, renders blood type mismatching between a blood bag and a patient physically impossible. The method and apparatus disclosed are readily implementable with existing procedures and equipment with little change or added expense.

Additional advantages of this invention will become apparent from the description which follows, taken in conjunction with the accompanying drawings.

BRIEF DESCRIPTION OF THE DRAWINGS

FIG. 3 is an exploded close up view showing the relationship of one set of the connectors to one another And to the blood bag;

FIG. 4 is an exploded view of another matching set of connectors according to the invention;

FIG. 5 is an exploded view of another matching set of connectors according to the invention;

FIG. 6 is an exploded view of another matching set of connectors according to the invention;

FIG. 7 is an exploded view of another matching set of connectors according to the invention;

FIG. 8 is an exploded view of another matching set of connectors according to the invention;

FIG. 9 is an exploded view of another matching set of connectors according to the invention;

FIG. 10 is an exploded view showing a set of connectors in relationship to one another and to an intravenous needle for insertion into a patient's arm;

FIG. 11 is a perspective view showing the various parts of FIG. 10 in operation; and FIG. 12 is a close up view showing the connectors of FIGS. 10 and 11 in relationship to one another.

BEST MODE FOR CARRYING OUT THE INVENTION

Figure 1:
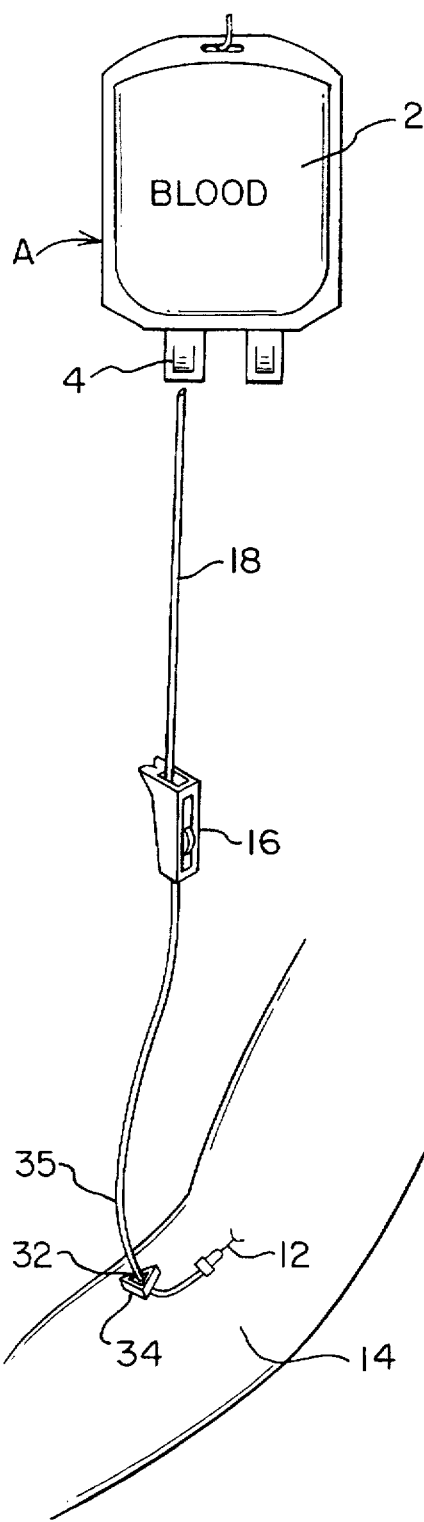
FIG. 1 is a perspective view of the configuration-coded connectors of the present invention in use in a typical blood transfusion system solely at the patient's arm.
Figure 2:
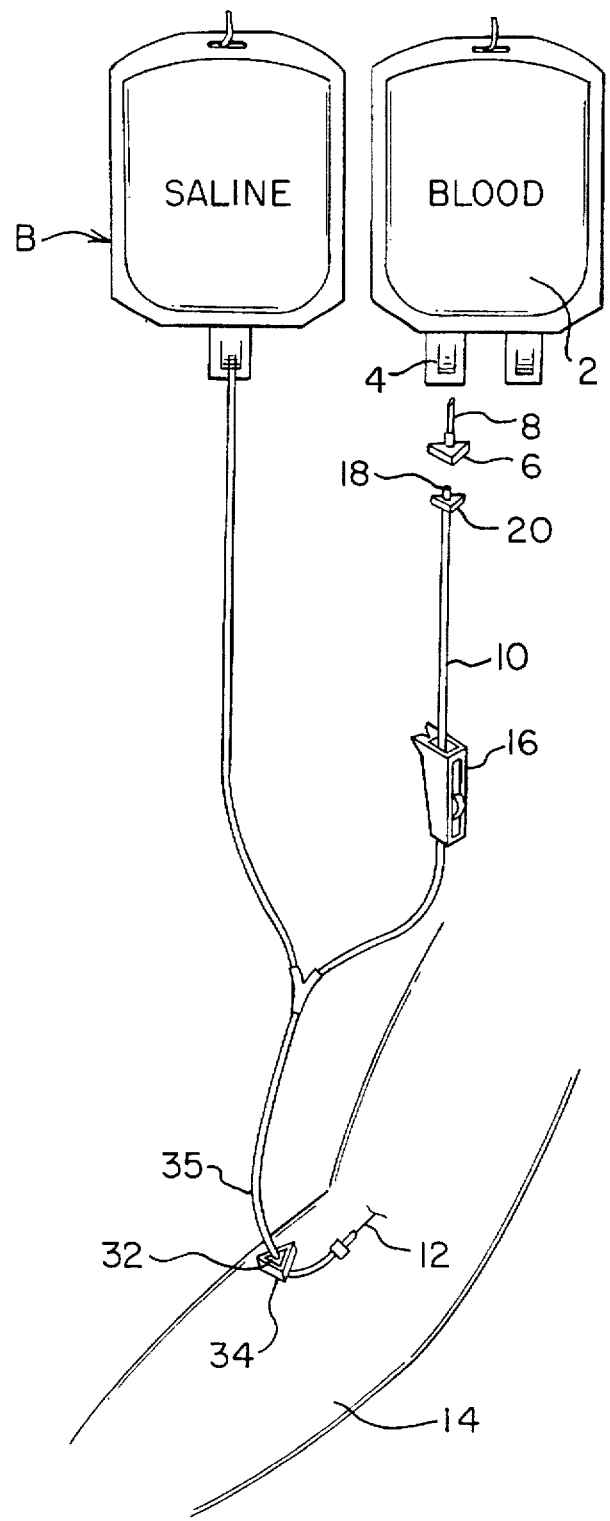
FIG. 2 is a perspective view of the connectors of the present invention in use both at the blood bag and at the patient's arm, in another typical blood transfusion/saline additive system.

Referring now to FIGS. 1 and 3, a complete blood transfusion system A is shown. In the system A, a blood bag 2 having an outlet 4 for removal of blood is provided. A female connector 6 has a sharpened tubular protrusion 8 for insertion into the outlet 4 to pierce the blood bag 2 and to provide access thereto. Blood tubing 10 extends from the bag 2 to connect with an intravenous needle 12 at the arm 14 of a patient.

A roll clamp 16 is provided to control the blood flow through the tubing 10. At the bag end 18 of the tubing, a male connector 20 is provided for mateably connecting with female connector 6. As may be seen in FIG. 3, male connector 20 and female connector 6 are configuration-coded in a matching way so that they may be sealably connected. If the configuration-codings of the connectors 6,20 do not match, connection will not be possible. As depicted in FIGS. 3 through 9, a total of seven pairs of matching configuration-coded connectors are provided. Each of the seven sets of connectors corresponds with one of the seven possible blood types to be protected against mismatching to a patient's blood type. (There are actually eight possible types of blood, but one type, 0-negative, is considered universally acceptable by all patients regardless of blood type.) None of the female connectors 6, 6a, 6b, 6c, 6d, 6e, 6f, are mateable with any of the male connectors 20, 20a, 20b, 20c, 20d, 20e, 20f, except for the particular connector which has the matching configuration coding, i.e., the connector from the same set, corresponding to the same blood type.

Referring now to FIG. 2 and FIGS. 10 through 12, there is depicted the use of configuration coded connectors 32,34 at the patient end 35 of the blood tubing 10. The female connector 34 is connected to a short length of tubing 36 which may be removably attached to the receiving port 38 of intravenous needle 12 by means of a cap 40. The cap 40 is typically threaded to screw onto the outer ridge 42 of the needle's receiving port 38. The male connector 32 matches the female connector 34 in the same fashion as described earlier for connectors 6,20. Ideally, male connector 32 would be identical in size and shape with connector 20. If the configure-codings of any one of the connectors does not match the configuration-coding of its intended mate, a connection is not possible and a mismatch is thereby prevented.

In use, the matching configuration-coded connectors may be selected and used in a variety of ways to prevent mismatching of blood between the blood bag and the patient. Since the intravenous needle 12 often remains in the arm of the patient for extended periods, selecting female connector 34 with configuration-coding matching the patient's blood type will effectively prevent the wrong type of blood from being administered. Another safeguard is to assure that the tubing 10 and its connectors 20,32 are properly selected to also match the patient's blood type. One effective way of assuring such proper selection is to attach the female connector 6 directly to the blood bag 2, so that the bag 2 and associated connector 6 are delivered together for use. This approach would essentially eliminate all human error other than those associated with matching the correct connector 6 to the blood type of the bag 2, or selection of the correct connectors 20,32,34 to match the blood type of the patient. However, these possible errors are more easily controllable than the currently existing possible errors. Selection of the proper connector 6 for the blood bag 2 could easily be checked and double checked at the source of the blood as it is packaged and labelled. Selection of the correct connector 34 for use at the arm of the patient could also be checked and double checked. However, once in place, the connector 34 would effectively eliminate any chance for further error in blood-type matching, assuming that the other connectors are properly selected.

Various other ways of using the connectors of the present invention to prevent blood-type mismatching are also feasible. Most notably, a single pair of matched connectors could be utilized, either at the bag end 18 or at the patient end 35 of the tubing 10. The effectiveness of such approaches would clearly depend upon the proper selection of the connectors. If a single pair of connectors 32,34 were to be utilized at the patient end 35 of the tubing 10, then tubing 10 might be packaged with the blood bag 2 to the correct selection of the connector corresponding to the blood-type of the bag. Similarly, if a single pair of connectors 6,20 were to be utilized at the bag end 18 of the tubing 10, then a supply of tubing 10 might be kept near the patient for use with each blood bag, which would be packaged with a selected female connector 6.

This invention has been described in detail with reference to a particular embodiment thereof, but it will be understood that various other modifications can be effected within the spirit and scope of this invention.

I claim:

1. An apparatus for preventing mismatching of blood types between a blood bag and a patient comprising:

a first connector for sealably connecting with an outlet of the blood bag, said connector having means for piercing the bag and allowing access thereto when inserted into the outlet, said connector further having a configuration-coding corresponding to the blood-type of the blood in the bag; and blood tubing for fluidly connecting with the bag through said first connector at a first end and with the patient at a second end, said tubing having a second connector at said first end, said second connector having a configuration-coding corresponding to the blood-type of the patient, said codings of said first and second connectors being necessarily matching in order to allow said connectors to sealably connect.

2. An apparatus for preventing mismatching of blood types between a blood bag and a patient as claimed in claim 1, further comprising:

a third connector at the second end of said tubing, said third connector having a configuration-coding corresponding to the patient's type;

inlet means on said tubing for administering blood to the patient; and a fourth connector sealably connectable to said inlet means, said fourth connector having a configuration coding corresponding to the blood-type of the patient, said codings of said third and fourth connectors being necessarily matching in order to allow said connectors to sealably connect.

3. An apparatus for preventing mismatching of blood types between a blood bag and a patient, comprising:

inlet means for sealably delivering blood to the patient;

a first connector sealably connectable to said inlet means, said connector having a configuration coding corresponding to the blood-type of the patient; and blood tubing for fluidly connecting with the bag through said first connector at a first end and with the patient at a second end, said tubing having a second connector at said second end for sealably connecting with said first connector, said second connector having a configuration coding corresponding to the blood-type of the blood in the bag, said codings of said first and second connectors being necessarily matching in order to allow said connectors to sealably connect.

* * * * *